US011376064B2

(12) United States Patent
Rankin (10) Patent No.: US 11,376,064 B2
(45) Date of Patent: Jul. 5, 2022

(54) APPARATUS AND METHOD FOR CARDIAC ABLATION

(71) Applicant: DOT MEDICAL LTD., Macclesfield (GB)

(72) Inventor: Ian Roderick Rankin, Macclesfield (GB)

(73) Assignee: DOT MEDICAL LTD., Macclesfield (GB)

( * ) Notice: Subject to any disclaimer, the term of this patent is extended or adjusted under 35 U.S.C. 154(b) by 593 days.

(21) Appl. No.: 16/306,211

(22) PCT Filed: Jun. 7, 2017

(86) PCT No.: PCT/GB2017/051645
§ 371 (c)(1),
(2) Date: Nov. 30, 2018

(87) PCT Pub. No.: WO2017/212257
PCT Pub. Date: Dec. 14, 2017

(65) Prior Publication Data
US 2019/0192223 A1    Jun. 27, 2019

(30) Foreign Application Priority Data

Jun. 7, 2016 (GB) ..................... 1609887

(51) Int. Cl.
*A61B 18/14* (2006.01)
*A61B 18/12* (2006.01)
(Continued)

(52) U.S. Cl.
CPC ...... *A61B 18/1492* (2013.01); *A61B 18/1206* (2013.01); *A61B 2017/00141* (2013.01);
(Continued)

(58) Field of Classification Search
CPC .......... A61B 2018/00636; A61B 2018/00642; A61B 2018/00648; A61B 2018/00654;
(Continued)

(56) References Cited

U.S. PATENT DOCUMENTS

2010/0023004 A1\* 1/2010 Francischelli ..... A61B 18/1442
606/41
2010/0036374 A1\* 2/2010 Ward ................. A61B 18/1206
604/23

(Continued)

FOREIGN PATENT DOCUMENTS

WO    WO 2015/171921 A2    11/2015

OTHER PUBLICATIONS

International Search Report dated Sep. 15, 2017, which issued in the corresponding Patent Application No. PCT/GB2017/051645.

*Primary Examiner* — Michael F Peffley
*Assistant Examiner* — Nicholas S Borsch
(74) *Attorney, Agent, or Firm* — Dickinson Wright PLLC (57) ABSTRACT

The invention comprises an apparatus for performing cardiac ablation by electroporation comprising: an applicator comprising a plurality of electrodes (16) each operable in use to supply an electrical potential across cells within an area of tissue (12); and a means to control the waveform of the electrical potential supplied by the plurality of electrodes, configured to provide a biphasic, truncated waveform with leading and trailing edges of differing magnitude.

22 Claims, 2 Drawing Sheets

(51) Int. Cl.
*A61B 18/00* (2006.01)
*A61B 17/00* (2006.01)

(52) U.S. Cl.
CPC .............. *A61B 2018/0016* (2013.01); *A61B 2018/00357* (2013.01); *A61B 2018/00577* (2013.01); *A61B 2018/00613* (2013.01); *A61B 2018/00702* (2013.01); *A61B 2018/00761* (2013.01); *A61B 2018/00839* (2013.01); *A61B 2018/1467* (2013.01)

(58) Field of Classification Search
CPC .......... A61B 2018/00666; A61B 2018/00672; A61B 2018/00678; A61B 2018/00702; A61B 2018/0072; A61B 208/00726; A61B 2018/00732; A61B 2018/0075; A61B 2018/00767; A61B 18/1492; A61B 18/1206; A61B 2018/00839; A61B 2017/00141; A61B 2018/00577; A61B 2018/1467; A61B 2018/0016; A61B 2018/00357; A61B 2018/00613; A61B 2018/00761; A61B 2018/00351; A61B 18/16; A61B 2018/00892; A61B 2018/00363; A61B 2018/00369; A61B 2018/00375

See application file for complete search history.

(56) References Cited

U.S. PATENT DOCUMENTS

| | | | |
|---|---|---|---|
| 2010/0152725 A1* | 6/2010 | Pearson | A61B 18/12 606/41 |
| 2011/0106221 A1* | 5/2011 | Neal, II | A61B 18/12 607/2 |
| 2011/0238062 A1* | 9/2011 | Koss | A61B 18/1206 606/34 |
| 2013/0303876 A1* | 11/2013 | Gelfand | A61B 18/1477 600/407 |
| 2016/0051324 A1 | 2/2016 | Stewart et al. | |
| 2017/0065339 A1* | 3/2017 | Mickelsen | A61N 1/327 |
| 2018/0193082 A1* | 7/2018 | Rubinsky | A61B 18/1402 |

* cited by examiner

APPARATUS AND METHOD FOR CARDIAC ABLATION

TECHNICAL FIELD OF THE INVENTION

The present invention relates to improvements in or relating to apparatus and methods for cardiac ablation, and in particular to apparatus and methods for cardiac ablation for the treatment of cardiac arrhythmias.

BACKGROUND TO THE INVENTION

Cardiac arrhythmias are common, particularly those which originate in the atrium of the heart. In any population of the world at least 1% will have an atrial arrhythmia, the most common of which is called atrial fibrillation (AF).

There are many treatments available to treat AF with varying degrees of aggression and success and include anti-arrhythmic medication and internal or external cardioversion (as is known in the art). Where such treatments are unsuccessful or only temporarily sustain normal sinus rhythm, then a more permanent solution is required and this typically comprises a cardiac ablation procedure. This is a much more time consuming (typically between 2 and 4 hours) and aggressive procedure. The purpose of cardiac ablation is to create scar lines (lesions) in the atrium which either prevent the initiation of AF or if AF is initiated, prevents the continued conduction of the AF across the tissues so that it peters out and terminates on its own.

Known energy sources used to create the lesions include radio frequency (RF), cryo-ablation energy (cryo), laser energy and ultrasound. By far the most common energy source is RF which essentially creates lesions by heating the tissue. This can be done by applying RF to tissue via the tip of a cardiac catheter placed in the heart. The tip is then moved to an adjacent position and a second application of RF is delivered which overlaps the first. By continuing this process it is possible to create a line of "burn spots" which altogether make a lesion line. As each application of RF takes a minute or more this is a time consuming process typically taking 2 to 4 hours to create enough lesions to prevent the AF. It is a highly skilled operation and completely dependent on the operator's ability to manipulate the catheter to specific positions in the heart.

To improve upon this technique, linear ablation catheters have been developed which allow delivery of RF along the edge of a catheter rather than just at the tip allowing a "linear burn" to occur rather than a "spot burn". The theory being that one application of RF can create a linear lesion in a much shorter time. A typical linear lesion catheter has a series of ring electrodes from which the RF energy disseminates. Each electrode has a means to measure temperature in the surrounding tissue such as a thermistor or thermocouple and can therefore control the amount of RF energy delivered to each ring electrode. However, in practice it has proven quite difficult to get a consistent linear lesion by this method mainly because of the difficulty in maintaining contact with tissue all along the length of the catheter adjacent to the cardiac tissue. Invariably a touch up is required using a spot burn catheter which reduces the advantages of the linear catheter leading to a decrease in use.

Cryo and laser energy systems are generally used to ablate around the ostia of the pulmonary veins (PV) in the left atrium, specifically to treat paroxysmal AF. Both cryo and laser catheters consist of a balloon on a catheter which is inserted in to each PV effectively plugging it and making contact around the ostia of the vein. The cryo catheter then delivers an extremely cold fluid in to the balloon which effectively freezes and ablates the cardiac cells in the vicinity of the PV ostium creating a lesion around a PV. The laser balloon shines a laser on to the tissue where the balloon makes contact with the ostium and heats the tissue to the point where the tissue is ablated and becomes non-conductive. In both systems the primary purpose is to create lesions around the PVs which are sufficient to allow termination of the AF.

Cryo and laser energy systems may not be effectively used successfully in a larger group of patients which are termed persistent AF (as opposed to paroxysmal AF). Persistent AF patients tend to have been in AF far longer than the paroxysmal AF patients and as such it is recognized that the physiology of the cardiac cells will have changed more dramatically.

A further technique known as electroporation consists of delivering high energy shocks and is used extensively in the oncology arena specifically for the treatment of tumours. When a high energy shock is delivered to a group of cells the surface membrane of the cells become permeable making cells able to absorb medications which they would not previously absorb. This technique is used to impregnate tumours, for example, with medications making them more likely to be treated than previously. It is widely known in oncology that if the energy delivered is too great then the cell membrane ruptures causing necrosis of the cell. Whilst necrosis of the cell is undesirable in cancer treatments, there is potential to use electroporation to cause necrosis of cells to create cardiac lesions. However, at present, no complete solution for the treatment of human heart conditions, in particular for AF (both persistent and paroxysmal), has been provided.

It would therefore be advantageous to provide a method of cardiac ablation which utilises electroporation of cells within the cardiac tissue.

It would also be advantageous to provide an apparatus for performing a method of cardiac ablation utilising electroporation of cells within the cardiac tissue; especially using optimised apparatus which is energy efficient yet provides excellent control and efficiency of ablation of heart tissue.

It is an aim of an embodiment or embodiments of the invention to overcome or at least partially mitigate the problems associated with the prior art.

SUMMARY OF THE INVENTION

According to a first aspect of the invention there is provided a method of cardiac ablation comprising the steps of:
  (a) locating an applicator within a heart; and
  (b) using a plurality of electrodes within the applicator to supply an electrical potential across cells within one or more areas of tissue within the heart; wherein the electrical potential supplied across the cells acts to rupture said cells to form a lesion within the tissue.

The method of the invention utilises electroporation of cells within the tissue of the heart to form lesions. Specifically, by applying an electrical potential across the cells, it is believed that the cell membranes of these cells become permeable which leads to the cells rupturing. The rupturing of the cells form a lesion within the tissue.

The applicator is typically located within a single chamber of the heart. The chamber may be a ventricle or atrium. Preferably, the method comprises locating an applicator within an atrium of the heart. In some embodiments the applicator may be located within the left side of the heart. In some embodiments the method may comprise locating the applicator within the left atrium of the heart to form a lesion within the tissue of the left atrium. It is known that ablating around or proximal to the ostia of the pulmonary veins in the left atrium using other, non-inventive techniques is associated with higher success rates in terminating atrial fibrillation. Therefore, by locating the applicator within the left atrium of the heart enables the method to be used to create lesions within the left atrium to treat atrial fibrillation, among other heart arrhythmias. In some embodiments the method may comprise locating the applicator within the left ventricle of the heart to form a lesion within the tissue of the left ventricle.

In other embodiments the applicator may be located within the right side of the heart. In some embodiments the method may comprise locating the applicator within the right atrium of the heart to form a lesion within the tissue of the right atrium, or may comprise locating the applicator within the right ventricle of the heart to form a lesion within the tissue of the right ventricle.

The method may comprise performing cardiac ablation to treat cardiac arrhythmia in a patient. In such embodiments, the method may comprise forming one or more lesions within tissue of the patient's heart to prevent or reduce the conduction of arrhythmia signals across or through the cardiac tissue of a patient. In some embodiments the method may comprise performing cardiac ablation to treat atrial arrhythmia in a patient. In some embodiments the method comprises performing cardiac ablation to treat atrial fibrillation in a patient.

In some embodiments the method may comprise using an applicator comprising a plurality of electrodes along its length. The plurality of electrodes may be equally spaced along the length of the applicator. In some embodiments, the method comprises using each electrode to supply an electrical potential across cells within an area of tissue of the heart which is proximal to the electrode to rupture cells within that area. In this way, the method comprises forming a plurality of ablation sites which in some embodiments may join to form a linear, or substantially linear lesion within the tissue.

The method may comprise using an applicator which comprises an elongate structure. In some embodiments, the applicator is tubular having a bore running through the applicator along at least a portion of its length. The applicator may comprise a bore running through the entire length of the applicator. In some embodiments the applicator comprises a catheter.

The method may comprise forming a lesion which is no more than 0.25 cm, 0.5 cm, 0.75 cm or 1 cm, or at least 1 cm, 2 cm, 3 cm, 4 cm, 5 cm, 6 cm, 7 cm, 8 cm or 10 cm in length, for example. The method may comprise forming a lesion which is between 0.5 cm and 5 cm, or between 1 cm and 4 cm, for example. The method may comprise forming a lesion which has a depth of no more than 0.1 mm, 0.2 mm, 0.5 mm or 1 mm, or at least 1 mm, 2 mm, 3 mm, 4 mm, 5 mm, 6 mm, 7 mm, 8 mm, 9 mm, 10 mm or 15 mm for example. The method may comprise forming a lesion which has a depth between 0.1 mm and 10 mm, or between 0.1 mm and 8 mm, between 1 mm and 10 mm or between 1 mm and 8 mm, for example.

In some embodiments the method may comprise synchronising the supply of electrical potential across the cells with the natural beat of the heart. For example, the method may comprise synchronising the supply of electrical potential across the cells with the ventricular beat of the heart. In some embodiments the method may comprising using one or more sensors to detect the ventricular beat. The one or more sensors may comprise a sense electrode within the applicator or may comprise a separate sensor which may be located within or on the heart, for example. The one or more sensors and plurality of electrodes may be electrically connected in order to synchronise the supply of electrical potential with the detected ventricular beat.

The method may comprise supplying an electrical potential of up to 10V, or at least 10V, 20V, 30V, 40V, 50V, 60V, 70V, 80V, 90V or 100V in magnitude across the cells within the tissue area, for example. The method may comprise supplying an electrical potential of up to 2500V, 2000V, 1500V, 1000V, 500V, 400V, 300V, 250V, 225V, 200V, 175V, 150V, or 125V in magnitude across the cells within the tissue area, for example. In some embodiments the method may comprise supplying an electrical potential of between 10V and 2500V, or between 20V and 2000V, or between 30V and 1500V, or between 40V and 1000V, or between 50V and 500V, or between 60V and 400V in magnitude across the cells within the tissue area, for example.

The magnitude of the electrical potential supplied across the cells may be constant or may be varied. In some embodiments, the magnitude of the electrical potential may be varied by up to 5V or 10V, or at least 10V, 20V, 30V, 40V, 50V, 60V, 70V, 80V, 90V, 100V, 150V, 200V, 250V, 500V or 1000V for example. In some embodiments the magnitude of the electrical potential supplied across the cells may be varied between a maximum value of approximately 100V and a minimum value of approximately 90V, 80V, 70V, 60V, 50V, 40V, 30V, 20V or 10V, for example. In other embodiments the magnitude of the electrical potential supplied across the cells may be varied between a maximum value of approximately 2000V and a minimum value of approximately 500V, 400V, 300V, 250V, 200V, 150V or 100V, for example.

In some embodiments the method may comprise forming a single lesion within the tissue of the heart. In other embodiments the method may comprise forming more than one lesion within the tissue of the heart. In such embodiments, the method may comprise forming a first lesion with the applicator in a first position within the heart and subsequently moving the applicator to a second position before repeating step (b) to form a second lesion at this second position. The method may comprise subsequently moving the applicator to a third, fourth, fifth or nth position and forming respective third, fourth, fifth or nth lesions within the tissue of the heart.

In some embodiments the method may comprise using an applicator which has a bore therethrough. Within the bore may be located a guidewire or stylet for controlling the position of the applicator within the heart. In some embodiments the applicator may comprise an anchoring device and the method may comprise using the anchoring device to anchor the applicator in position within the heart.

The electrical potential may be supplied continuously across the cells within the area of tissue. In other embodiments the electrical potential may be supplied across the cells intermittently. The electrical potential may be supplied across the cells in a pulse. When used here and throughout the specification, the term "pulse" is intended to mean an application of an electrical potential across the cells for a given duration.

The electrical potential supplied across the cells may be defined by a waveform defining the value of the electrical potential supplied as a function of time. In some embodiments the method may comprise controlling the waveform of the electrical potential to control the electrical potential supplied across, and hence the total energy supplied to the cells. In such embodiments, the method may comprise using a waveform generator to control the electrical potential supplied across the cells.

The waveform of the electrical potential supplied across the cells may comprise a truncated waveform. In such embodiments, the truncated waveform comprises substantially instantaneous rises or falls in the magnitude of the electrical potential at the beginning and at the end of a pulse. These may form respective leading and trailing edges of the waveform. In some embodiments the method may comprise defining the position of at least one leading edge and at least one trailing edge of the waveform of the electrical potential supplied across the cells. Defining the trailing edge of the waveform may truncate the waveform.

In some embodiments the electrical potential may be supplied across the cells at a constant magnitude for the duration of a pulse. In such embodiments, the waveform of the pulse may comprise a simple square wave wherein the electrical potential supplied across the cells is initially set at a given value (defined by a leading edge of the square waveform), kept at this given value for a set period of time (corresponding to the width of the square waveform) and then reduced to a base value, which may be but is not necessarily at 0V, at the end of the pulse (defined by a trailing edge of the square waveform).

In other embodiments, the method may comprise varying the magnitude of the electrical potential supplied during a pulse. The variation in the magnitude of the electrical potential may comprise raising the magnitude from a base value (which may be 0V) to a maximum value over a given length of time, which may be the duration of the pulse. Additionally or alternatively, the variation in the magnitude of the electrical potential may comprise reducing the magnitude from a maximum value to a base value (which again may be 0V) over a given length of time, which may be the duration of the pulse.

In presently preferred embodiments the method comprises initially raising the magnitude of the electrical potential from a base value to the first value, allowing the magnitude of the electrical potential to decay over the duration of the pulse to a second value, before reducing the magnitude from the second value to the base value at the end of the pulse. The magnitude of the electrical potential supplied across the cells may decay at a rate which is proportional to the impedance of the tissue being treated. The raising of the electrical potential from the base value to the first value may comprise a leading edge of the associated waveform, whereas reducing the magnitude of the electrical potential from the second value to the base value comprises a trailing edge of the associated waveform.

By controlling the relative size and/or separation (in time) of the leading and trailing edges of such a waveform, the method comprises a means to control the magnitude of electrical potential supplied across the cells of the tissue as a function of time. In some embodiments the method comprises utilising the waveform generator to control the relative size and/or separation of the leading and trailing edges of the associated waveform.

However, as discussed above, the relative sizes of the leading and trailing edges of the waveform, and hence the decay rate of the electrical potential across the cells will generally be dependent on the impedance of the tissue being treated. Therefore, in some embodiments the method comprises controlling the separation (in time) of the leading and trailing edges only, by controlling when the waveform is truncated (i.e. at what point during the pulse the magnitude of the electrical potential is reduced to a base value). The method may comprise truncating the waveform after the magnitude of the electrical potential has decayed by a pre-determined amount. This may comprise an absolute value decrease, i.e. after a decrease of a pre-determined number of volts, or may comprise a percentage decrease from an initial value. The percentage drop-off of the electrical potential may be defined as the "tilt" of the corresponding waveform, and may be calculated from the relative sizes of the leading and trailing edges. Additionally or alternatively, the waveform may be truncated after a given length of time. In some embodiments the impedance of the tissue being treated may be such that the electrical potential supplied across the cells in the tissue would never reduce by the predetermined amount, or would not reduce within an acceptable time period. In such instances it is therefore necessary to truncate the waveform after a given length of time.

The "tilt" of the waveform may be calculated from the relative sizes of the leading and trailing edges relative to a base value. It is typically defined as the percentage drop off between the leading and trailing edge relative to a base value. In some embodiments the method comprises choosing the tilt of the waveform to determine at what point the waveform is truncated and hence at what point the electrical potential supplied across the cells of the tissue is reduced to a base value. The tilt value may be chosen to be up to 10%, or may be at least 10%, 20%, 30%, 40%, 50%, 60%, 70%, 80% or 90%, for example. The tilt of the waveform may be pre-programmed prior to step a) or step b).

In some embodiments the waveform may be truncated after a given length of time. This may comprise up to 1 ms, or at least 1 ms, 2.5 ms, 5 ms, 7.5 ms, 10 ms, 15 ms, 20 ms, 25 ms, 30 ms, 40 ms, 50 ms, 75 ms or 100 ms, for example. In some embodiments the waveform may be truncated after between 1ms and 100 ms, or between 2.5 ms and 50 ms, or between 5 ms and 25 ms, or between 5 ms and 10 ms, for example. In some embodiments the method may comprise truncating the waveform when it reaches a tilt value of between 40-60% or after 6-10 ms, for example, whichever occurs earliest.

In embodiments wherein the waveform of the electrical potential supplied to the cells is allowed to decay over the duration of the pulse, the decay may be linear with time. In other embodiments the decay of the electrical potential may as a non-linear function of time. For example, in some embodiments the electrical potential may decay exponentially with time over the duration of a pulse.

In some embodiments the waveform of the supplied electrical potential may be biphasic, that is, it may comprise both a positive phase and a negative phase, with the positive phase being defined where the value of the electrical potential supplied across the cells is positive with respect to a base value and the negative phase being defined where the value of the electrical potential supplied across the cells is negative with respect to the same base value. Preferably, the waveform comprises a positive phase immediately followed by a negative phase, however, in other embodiments the waveform may comprise a negative phase followed by a positive phase. In some embodiments, the second phase of the biphasic waveform may be initiated upon truncation of the first phase of the waveform.

The waveform may be antisymmetric about a midpoint of the waveform. For example, the duration and/or magnitude of the waveform may be equal on either side of the midpoint. In other embodiments the magnitude and/or duration of the positive and negative phases of the waveform may be different such that the biphasic waveform is asymmetric.

In some embodiments both the positive and negative phases of the biphasic waveform may be truncated and comprise leading and trailing edges. The leading edge of both the positive and negative phases may have the same, or substantially the same magnitude. Similarly, the trailing edge of both the positive and negative phases may have the same, or substantially the same magnitude. However, in presently preferred embodiments the trailing edge of the positive phase of the waveform is equal in magnitude to the leading edge of the negative phase of the waveform. In such embodiments, the leading edge of both the positive and negative phases may be greater than the corresponding trailing edge such that the magnitude of the electrical potential decays during the positive phase, the electrical potential switches orientation at an intermediate point within the pulse, and then continues to decay during the negative phase.

The positive and/or negative phases of the waveform may each be truncated upon reaching a given tilt value, or after a given length of time as is required. In some embodiments the tilt value and/or time at which the positive and negative phases of the waveform are truncated may be equal. However, in presently preferred embodiments the method comprises individually selecting the tilt value and/or time at which the positive and negative phases of the waveform are truncated.

According to a second aspect of the present invention there is provided a method of cardiac ablation comprising the steps of:
(a) locating an applicator within a chamber of a heart; and
(b) using a plurality of electrodes within the applicator to supply an electrical potential across cells within one or more areas of tissue within the heart to rupture said cells to form a lesion within the tissue; wherein the waveform of the electrical potential supplied across the cells comprises a biphasic waveform.

The applicator may be located within a single chamber of the heart. The chamber may be a ventricle or atrium. Preferably, the method comprises locating an applicator within an atrium of the heart. In some embodiments the applicator may be located within the left side of the heart. In some embodiments the method may comprise locating the applicator within the left atrium of the heart to form a lesion within the tissue of the left atrium, or may comprise locating the applicator within the left ventricle of the heart to form a lesion within the tissue of the left ventricle. In other embodiments the applicator may be located within the right side of the heart. In some embodiments the method may comprise locating the applicator within the right atrium of the heart to form a lesion within the tissue of the right atrium, or may comprise locating the applicator within the right ventricle of the heart to form a lesion within the tissue of the right ventricle.

The second aspect of the invention may comprise any or all of the features of the first aspect of the invention as is desired or is appropriate.

According to a third aspect of the invention there is provided an apparatus for performing cardiac ablation comprising: an applicator comprising a plurality of electrodes each operable in use to supply an electrical potential across cells within an area of tissue; and a means to control the waveform of the electrical potential supplied by the plurality of electrodes.

The means to control the waveform of the electrical potential supplied by the plurality of electrodes may be configured to provide a biphasic, truncated waveform with leading and trailing edges of differing magnitude.

In some embodiments the applicator comprises a plurality of electrodes along its length. The electrodes may be equally spaced along the length, or along at least a portion of the length of the applicator. Each of the plurality of electrodes may comprise a ring electrode.

In some embodiments each of the plurality of electrodes may be electrically connected to one another. The electrical connection may comprise a wire or the like contained within the applicator. In other embodiments, each of the plurality of electrodes may be independently connected to an electrical source and not to one or more other electrodes. In this way, the electrical potential supplied by each electrode, in use, may be controlled independently of the other electrodes. In some embodiments the plurality of electrodes may be electrically connected in groups consisting of one or more individual electrodes. In such embodiments, the electrical potential supplied by each group of electrodes, in use, may be controlled independently of the other electrode groups.

In some embodiments the applicator comprises an elongate structure. The applicator may comprise a bore therethrough. There may be provided a guidewire or stylet through the bore in the applicator which is operable in use to be used to control the position of the applicator. The guidewire or stylet may additionally comprise an anchoring point thereon. The anchoring point may be operable in use to attach the applicator to a portion of the tissue being treated to prevent movement of the applicator during treatment.

The apparatus may additionally comprise a means to ground the electrical connections present. The grounding means may comprise a further applicator arranged to be located within or proximal to the heart being treated, in use. In other embodiments the grounding means may comprise a back plate which may be connected to the surface of the skin of a patient being treated, in use.

In some embodiments the means to control the waveform of the electrical potential supplied by the plurality of electrodes may be operable to control the extent and duration of the electrical potential supplied via the electrodes. The means to control the waveform of the electrical potential may comprise means configured to provide a biphasic, truncated waveform with leading and trailing edges of differing relative magnitude (tilt). The biphasic, truncated waveform may be an antisymmetric, biphasic truncated waveform and/or may be an asymmetric, biphasic truncated waveform. An apparatus which is configured to provide electrical potential across cells in the form of a biphasic, truncated waveform with tilt is particularly energy efficient whilst providing excellent control of ablation and rupturing of cells in heart tissue. For example, in some embodiments the means to control the waveform of the electrical potential may be operable, in use, to define the tilt or desired tilt (i.e. the relative sizes of leading and trailing edges of the waveform with respect to a base value) at which the waveform is truncated. The means to control the waveform of the electrical potential may be operable, in use, to define the separation of the leading and trailing edges of the waveform to define the duration of the pulse of electrical potential to be supplied.

In some embodiments the means to control the waveform of the electrical potential supplied by the plurality of electrodes may comprise a waveform generator.

The apparatus may additionally comprise a user interface. The user interface may be operable in use to receive inputs from a user. The inputs may define the shape of the waveform of the electrical potential supplied via the electrodes, in use. The inputs may relate to the duration of the pulse of electrical potential supplied via the electrodes, the magnitude of the electrical potential supplied via the electrodes and or the tilt or desired tilt at which the waveform is truncated, in use. The user interface may be electrically connected to the waveform generator.

The user interface may additionally be operable to display to a user the operational state of the apparatus. For example, in some embodiments the user interface may display to a user the magnitude of the electrical potential being supplied, the duration for which the electrical potential is or has been supplied, the total energy supplied to the cells of a user, or the waveform of the electrical potential itself The applicator may additionally comprise a sensor electrode. The sensor electrode may be operable in use to detect one or more electrical signals. The one or more electrical signals may comprise the electrical signals running through the tissue being treated. In some embodiments the sensor electrode may be operable to detect one or more electrical signals may comprise electrical signals from the sinoatrial node of a heart being treated. The sensor electrode may be electrically connected to the waveform control means. In such embodiments, the waveform control means may be operable to control the electrical potential supplied via the plurality of electrodes upon detection of an electrical signal by the sensor electrode, in use. In such embodiments, the waveform control means may be operable to synchronise the supply of electrical potential via the electrodes with the natural beat, which may be the ventricular beat, of the heart being treated.

The apparatus of the third aspect of the invention may be used in a method of the first or second aspect of the invention, and the electrodes, applicator, and waveform control means may be configured to provide each method step described hereinabove.

DETAILED DESCRIPTION OF THE INVENTION

In order that the invention may be more clearly understood embodiments thereof will now be described, by way of example only, with reference to the accompanying drawings, of which.

Figure 1:
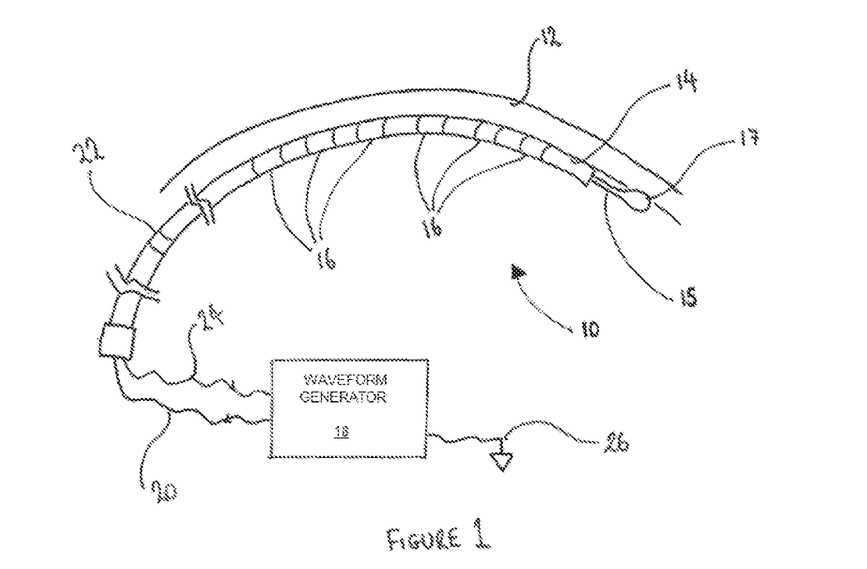
FIG. 1 is a schematic diagram of an embodiment of an apparatus in accordance with the present invention.
Figure 2:
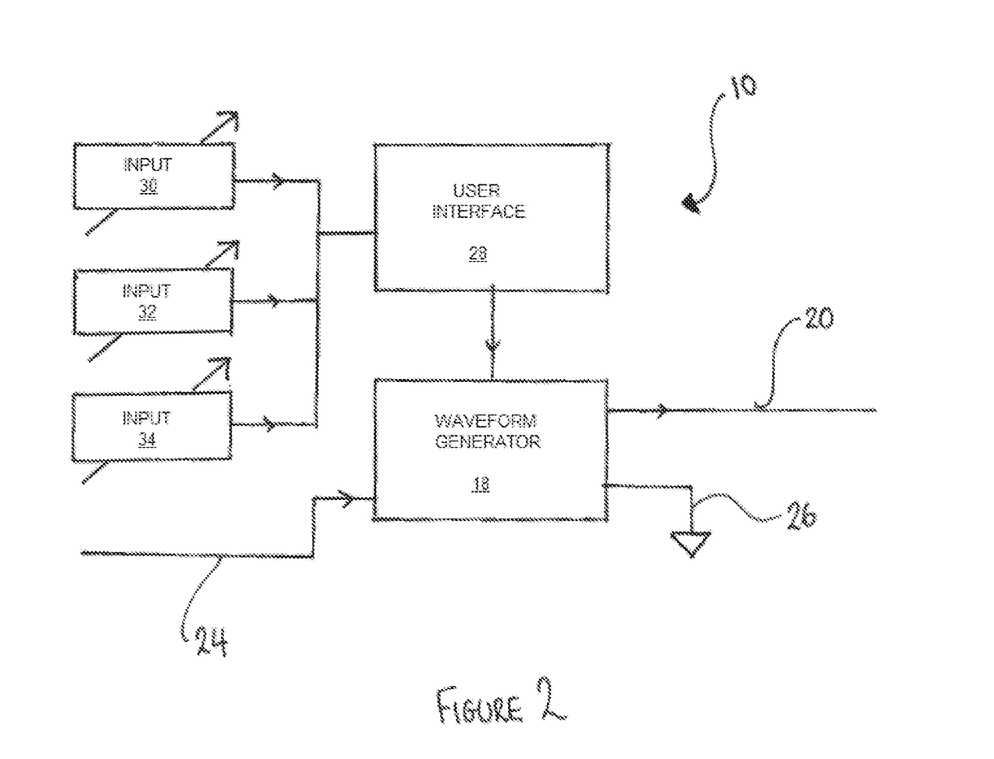
FIG. 2 is a further schematic diagram of an embodiment of an apparatus in accordance with the present invention.

FIGS. 1 and 2 are a schematic diagrams of an embodiment of an apparatus 10 for performing cardiac ablation in accordance with the invention. The apparatus 10 is shown in position proximal to a wall of cardiac tissue 12 and comprises an elongate applicator in the form of a catheter 14 which has a plurality of ring electrodes 16 spaced along its length. As will be discussed in detail below, the electrodes 16 are operable to supply an electric potential across cells within the cardiac tissue 12 to ablate the cells to form one or more lesions within the tissue 12.

The electrodes 16 are electrically connected to a waveform generator 18 via an electrical connection 20, which will typically comprise a wire or the like. The waveform generator 18 is operable in use to control the waveform of the electrical potential supplied by the electrodes 16, as described below. In addition, the catheter 14 comprises a sensor electrode 22 which is operable in use to detect electrical signals within the tissue 12 itself. These electrical signals will typically be signals relating to the ventricular beat of the heart being treated. The sensor electrode 22 is electrically connected to the waveform generator 18 via electrical connection 24. In this way, the electrical potential supplied by the electrodes 16 across the cells within the tissue 12 may be synchronised with the electrical signals detected by the sensor electrode 22. The waveform generator 26 is also connected to ground via connection 26. The ground connection may comprise a back plate or further catheter (not shown) within or within the vicinity of the catheter 14.

The illustrated catheter 14 has a bore therethrough (not shown) which houses a guidewire 15 for controlling the position of the catheter 14, in use. In addition, the guidewire 15 includes an anchoring tip 17 at an end thereof. The anchoring tip 17 is operable in use to anchor the catheter 14 to the tissue 12 to prevent the catheter 14 from moving during treatment and may be an anchoring tip as described in International PCT Application No. WO2006/010908 A1.

As shown in FIG. 2, the apparatus 10 additionally includes a user interface 28. The user interface 28 is operable in use to input instructions to the waveform generator 18 to control the waveform of the electrical potential supplied to the cells in the tissue 12. FIG. 2 shows inputs 30, 32 and 34 which may correspond to the magnitude of the electrical potential supplied, the "tilt" (i.e. the amount by which the electrical potential decays or is desired to decay over the duration of a pulse) and the duration of the pulse itself. Each of these values may be input via the user interface 28 into the waveform generator 18 before or during the treatment process.

The operational use of the apparatus 10 and embodiments of a method in accordance with the invention will now be described with reference to the Figures.

Initially, the catheter 14 is located within a chamber of the heart and positioned proximal to the wall of cardiac tissue 12 (as shown in FIG. 1). When in this position, the ring electrodes 16 are used to supply an electrical potential across cells within the tissue 12. The extent and duration of the supply of an electrical potential across the cells is controlled by the waveform generator 18 which is in turn controlled by a user inputting instructions via user interface 28. The sensor electrode 22 is operable to inform the generator 18 when an electrical signal has been detected such that the electrical potential supplied by the ring electrodes 16 is synchronised with the ventricular beat of the heart being treated.

Supplying an electrical potential across the cells within the tissue 12 causes the cell membrane to become permeable and ideally rupture leading to cell necrosis. The overall effect of the cell membranes rupturing is the formation of a lesion within the tissue 12 and in the illustrated embodiment, a linear lesion corresponding to the length of the catheter 14 between the first and last electrodes 16.

This process may be repeated one or more additional times at different locations on the cardiac tissue 12 to form one or more additional lesions therein.

Figure 3:
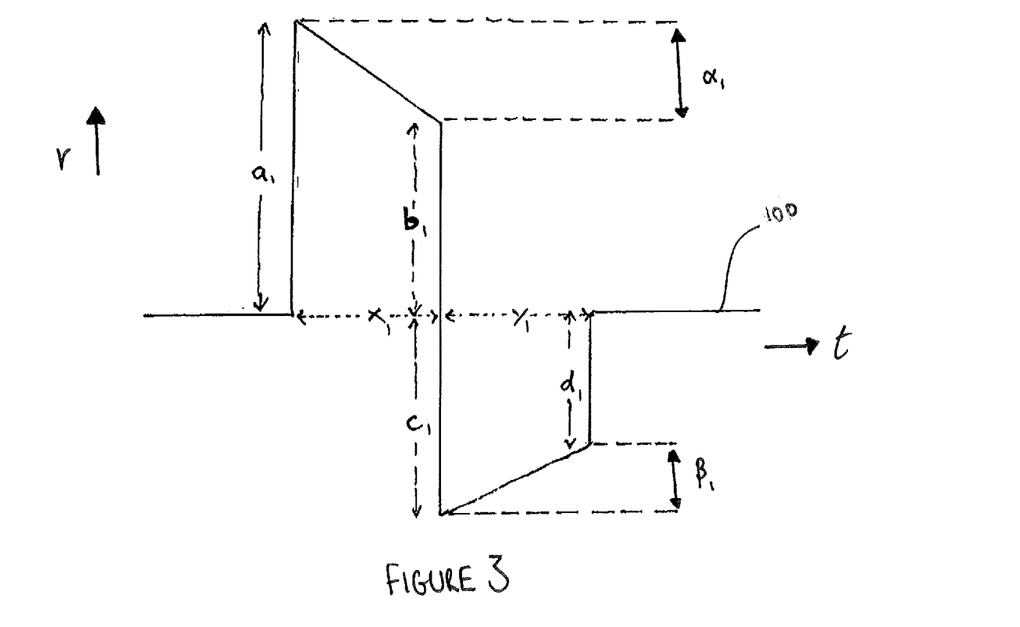
FIG. 3 is a graphical representation illustrating an exemplary waveform of the electrical potential supplied to cells when performing an embodiment of the method of the present invention.
Figure 4:
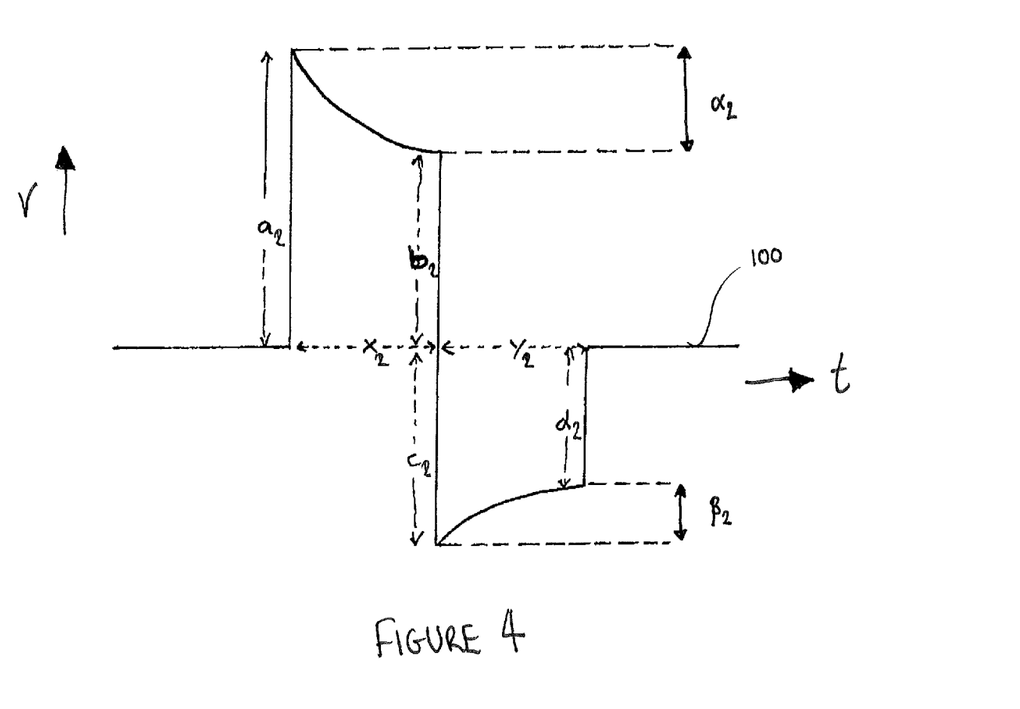
FIG. 4 is a further graphical representation illustrating an exemplary waveform of the electrical potential supplied to cells when performing an embodiment of the method of the present invention.

The electrical potential will typically be supplied across the cells in the tissue 12 in the waveform shown in FIG. 3 or FIG. 4, which illustrate how the voltage V of the electrical potential across the cells varies with time t. The waveforms shown illustrate a single electrical pulse supplied to the cells within the tissue 12. Both FIGS. 3 and 4 illustrate biphasic waveforms with FIG. 3 showing the ideal waveform and FIG. 4 showing a waveform which is typically achieved in practice. As discussed above, the shape of the waveforms is controlled by the operation of the waveform generator 18 under the instruction of the user inputs at the user interface 28.

Each of the illustrated waveforms are biphasic and include a positive phase followed by a negative phase (relative to a base value 100). The positive phase is defined by a leading edge a and a trailing edge b separated by a time x. Similarly, the negative phase is defined by a leading edge c and a trailing edge d separated by a time y. The leading edges a, c are the instance where the electrical potential is raised from the base value 100 defining the beginning of the corresponding phase of the waveform. The trailing edges b, d are the instances where the electrical potential is reduced to the base value 100 at the end of the corresponding phase of the waveform.

In each phase, the magnitude of the electrical potential decays such that the height of the leading edge a, c is greater than the height of the corresponding trailing edge b, d. The rate at which the electrical potential decays is primarily dependent on the impedance of the tissue 12 being treated and will therefore vary between patients. The difference between the waveforms shown in FIGS. 3 and 4 is how the magnitude of the electrical potential decays in each phase. In FIG. 3, the decay is linear whereas in FIG. 4, the decay is non-linear. The non-linear decay is what is typically achievable and observed in practice.

The difference in magnitude between the leading and trailing edges may be quantified by calculating the percentage drop off in the voltage value of the electrical potential. As discussed above, this is typically referred to as the "tilt" of the waveform. With reference to the positive phase of the waveforms, the tilt, α, is calculated as follows:

$$\alpha(\%) = \left(\frac{a-b}{a}\right) \times 100 \quad \text{[Equation 1]}$$

A similar calculation may be performed to calculate the tilt, β, of the negative phase of the waveforms:

$$\beta(\%) = \left|\left(\frac{c-d}{c}\right)\right| \times 100 \quad \text{[Equation 2]}$$

In use, a user may input into the user interface 28 a desired tilt value α, β at which the waveform is to be truncated and hence at which point the electrical potential applied to the cells is to be removed (or switched to a corresponding negative value). The values of the tilt α, β may be chosen to be the same or may be chosen independently depending on the circumstances. Additionally or alternatively, a user may input into the user interface 28 a desired duration x, y of the positive and/or negative phases of the waveform, thereby defining the total duration of the pulse. The duration of the positive phase x may or may not be equal to the duration of the negative phase y. Ideally, the waveform will be truncated at a given tilt value, however, by also inputting a maximum duration of the positive and negative phases of the waveform, the waveform is prevented from running indefinitely in situations where the magnitude of the electrical potential supplied across the cells would never reduce by the desired amount as a result of the impedance of the tissue 12.

In this exemplary embodiment, the catheter 14 is introduced into the left atrium of the heart and positioned proximal to the wall of cardiac tissue 12 (as shown in FIG. 1). In some instances, the catheter 14 may be anchored to the wall of the cardiac tissue 12 via anchoring tip 17. As discussed above, when in this position, the ring electrodes 16 are used to supply an electrical potential across cells within the tissue 12.

In this embodiment, the electrical potential is supplied across the cells in the tissue 12 in a waveform similar to that shown in FIG. 4 and this is controlled by the operation of the waveform generator 18 under the instruction of the user inputs at the user interface 28. Specifically, a user will input values for the leading edges a, c of the positive and/or negative phases, the desired tilt α, β at which the relevant phase of the waveform is to be truncated and/or the maximum duration of the whole pulse (x+y) or each individual phase x, y. In this embodiment, a user may input a value for the leading edge a of the positive phase of the waveform to be 100V, a desired tilt value α, β for both phases to be 50% and a maximum duration for each phase x, y to be 8 ms. Upon initiation, the electrical potential supplied across the cells will rise quickly to 100V (with respect to the base value 100) and then begin to decay (as energy is dissipated within the tissue). The electrical potential will continue to decay until it reaches 50V (corresponding to the tilt value α of 50%) or until the positive phase has lasted for 8 ms, whichever occurs earliest. At this point, the electrical potential will switch orientation (corresponding to a truncation of the positive phase of the waveform and a beginning of the negative phase). Typically, the leading edge c of the negative phase is equal in magnitude to the trailing edge b of the positive phase, although this may not always be the case. However, in such instances, the leading edge c of the negative phase will be at −50V with respect to the base value 100 and will decay for the duration of the negative phase. Again, in this embodiment, the electrical potential will continue to decay until it reaches −25V (corresponding to the tilt value β of 50%) or until the positive phase has lasted for 8 ms, whichever occurs earliest. At this point, the negative phase of the waveform is truncated and the electrical potential supplied across the cells is returned to the base value, which will typically be 0V.

The above embodiments are described by way of example only. Many variations are possible without departing from the scope of the invention as defined in the appended claims.

The invention claimed is:

1. An apparatus for performing cardiac ablation comprising: an applicator comprising a plurality of electrodes each operable in use to supply an electrical potential across cells within an area of tissue; and a waveform generator configured to generate a waveform of the electrical potential supplied by the plurality of electrodes, wherein the waveform comprises a biphasic, truncated waveform with leading and trailing edges of differing magnitude and the waveform generator is programmed to truncate the waveform after the magnitude of the electrical potential has decayed by a pre-determined amount.

2. An apparatus of claim 1 wherein the applicator comprises a plurality of electrodes along its length.

3. An apparatus of claim 1 wherein the waveform generator is configured to control the extent and duration of the electrical potential supplied via the electrodes, in use.

4. An apparatus as claimed in claim 1 wherein the waveform generator includes a programmable tilt generator.

5. An apparatus as claimed in claim 1 wherein the waveform generator to control the waveform of the electrical potential is configured to provide an antisymmetric or asymmetric waveform.

6. An apparatus of claim 1 further comprising a user interface.

7. An apparatus of claim 6 wherein the user interface is operable in use to receive inputs from a user to define the shape of the waveform of the electrical potential supplied via the electrodes, in use.

8. An apparatus of claim 1 further comprising a sensor electrode operable in use to detect one or more electrical signals.

9. An apparatus of claim 8 wherein the sensor electrode is operable to detect electrical signals from a sinoatrial node of a heart being treated.

10. An apparatus of claim 9 wherein the sensor electrode is electrically connected to the waveform generator and the waveform generator is operable to control the electrical potential supplied via the plurality of electrodes upon detection of an electrical signal by the sensor electrode.

11. An apparatus of claim 1, wherein the pre-determined amount is defined as a percentage decrease from an initial value of the magnitude of the electrical potential relative to a base value.

12. A method of cardiac ablation comprising the steps of:
    (a) locating an applicator within a heart;
    (b) using a plurality of electrodes within the applicator to supply an electrical potential across cells within one or more areas of tissue within the heart;
    wherein the electrical potential supplied across the cells acts to rupture said cells to form a lesion within the tissue; and
    the method further comprises:
    controlling the waveform of the electrical potential to control the electrical potential supplied across the cells; defining the position of at least one leading edge and at least one trailing edge of the waveform of the electrical potential supplied across the cells, wherein defining the trailing edge of the waveform truncates the waveform after the magnitude of the electrical potential has decayed by a pre-determined amount.

13. A method of claim 12 wherein the applicator is located within the left side of the heart.

14. A method of claim 13 wherein the applicator is located within the left atrium of the heart to form a lesion within the tissue of the left atrium.

15. A method of any of claim 12 wherein the plurality of electrodes are provided along a length of the applicator.

16. A method of claim 12 further comprising synchronizing the supply of electrical potential across the cells with the electrical signal from a sinoatrial node of the heart.

17. A method of claim 12 wherein the pre-determined amount is a tilt value defined as a percentage decrease from an initial value of the magnitude of the electrical potential relative to a base value.

18. A method of claim 12 further comprising truncating the waveform after a given length of time.

19. A method of claim 12 wherein the waveform of the electrical potential supplied to the cells is biphasic comprising both a positive and negative phase.

20. A method of claim 19 wherein the waveform comprises a positive phase immediately followed by a negative phase.

21. A method of claim 20 wherein truncation of the positive phase initiates the negative phase of the waveform.

22. A method of claim 19 wherein at least one of the positive and negative phases of the waveform are each truncated upon reaching a given tilt value or after a given length of time.

* * * * *